United States Patent
Smith et al.

(10) Patent No.: US 8,147,477 B2
(45) Date of Patent: Apr. 3, 2012

(54) MIXING TOOL

(75) Inventors: Christine Smith, San Diego, CA (US); Rey Halili, San Diego, CA (US); Hong Qi, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/597,352

(22) PCT Filed: Apr. 25, 2008

(86) PCT No.: PCT/US2008/061653
§ 371 (c)(1),
(2), (4) Date: Mar. 26, 2010

(87) PCT Pub. No.: WO2008/134570
PCT Pub. Date: Nov. 6, 2008

(65) Prior Publication Data
US 2010/0191182 A1    Jul. 29, 2010

Related U.S. Application Data

(60) Provisional application No. 60/914,470, filed on Apr. 27, 2007.

(51) Int. Cl.
*A61M 5/32*    (2006.01)
(52) U.S. Cl. ..................................................... 604/414
(58) Field of Classification Search ............ 604/403, 604/411, 414, 415, 416; 141/26, 27
See application file for complete search history.

(56) References Cited

U.S. PATENT DOCUMENTS

| | | | |
|---|---|---|---|
| 3,552,387 A | 1/1971 | Stevens | |
| 5,241,969 A | 9/1993 | Carson et al. | |
| 5,385,547 A | 1/1995 | Wong et al. | |
| 5,466,220 A | 11/1995 | Brenneman | |
| 5,487,738 A * | 1/1996 | Sciulli | 604/414 |
| 5,649,912 A * | 7/1997 | Peterson | 604/187 |
| 6,162,199 A | 12/2000 | Geringer | |
| 6,497,697 B1 * | 12/2002 | Cohn | 604/414 |
| 7,140,401 B2 * | 11/2006 | Wilcox et al. | 141/2 |

FOREIGN PATENT DOCUMENTS

| | | |
|---|---|---|
| WO | WO 00/29049 | 5/2000 |
| WO | WO 02/053087 | 7/2002 |
| WO | WO 2005/041846 | 5/2005 |
| WO | WO 2005/048842 | 6/2005 |

* cited by examiner

*Primary Examiner* — Nicholas Lucchesi
*Assistant Examiner* — Aarti B Berdichevsky
(74) *Attorney, Agent, or Firm* — Christie, Parker & Hale, LLP (57) ABSTRACT

The present invention provides devices and methods for mixing a formulation containing two or more constituents, such as a drug product and a diluent. The devices have a chamber for securing a container of the drug product. Various embodiments are presented. In one embodiment the device has two or more sides connected by a hinge, the two or more sides defining the chamber between them, and a handle for grasping and manipulating the device. In another embodiment the device has a housing with two or more side bars defining the chamber, the container being visible from outside the housing between the side bars and having a stopping element at the distal end, and a handle having two arms for grasping.

20 Claims, 6 Drawing Sheets

MIXING TOOL

This application is the National Stage of International Application No. PCT/US2008/061653, filed Apr. 25, 2007, which claims the benefit of U.S. provisional application No. 60/914,470, filed Apr. 27, 2007, each of which is hereby incorporated by reference in its entirety, including all tables, figures, and claims.

TECHNICAL FIELD

Tools for mixing drug formulations

BACKGROUND OF THE INVENTION

The preparation of a drug formulation for injection often requires the user to mix a drug with a diluent immediately prior to injection. This mixing step is a requirement for drugs known to have a relatively short shelf life in solution. For example, a drug comprising microspheres generally requires mixing with a diluent before administration. The dry microspheres of the drug are initially contained in a sealed vial, and the diluent is transferred from a syringe to the vial via an adaptor, which acts as a coupler between the syringe and the vial. With the diluent and microspheres in the vial, the user is directed to shake the syringe/vial adaptor/vial assembly (e.g., for approximately thirty seconds) to resuspend the microspheres in the diluent. The drug formulation can then be collected by syringe in the assembly and administered subcutaneously via a needle injection.

The mixing step is a critical step in the drug preparation that can be difficult for some patients to execute properly or efficiently. Generally, the syringe, vial adaptor, and vial are individually sealed but packaged together in a kit. Once the patient puts the syringe/vial adaptor/vial assembly together, the components cannot be separated until the product is mixed. Removing any of the components from the assembly prior to shaking exposes the contents of the vial to the ambient surrounding. Additionally, the assembly process creates a permanent hole in the vial seal through which the contents can leak out. The sealed assembly can be difficult to handle, and the duration and vigorousness of the shaking required for mixing can be difficult for some patients, especially those with arthritis or limited mobility/strength in their hands and arms. Furthermore, because the vial in the assembly typically constitutes one or more effective doses of the drug, a vial mistakenly dropped or damaged during the mixing step can be very costly to the user.

A variety of mixing devices for drug/diluent formulations have been proposed to facilitate the mixing of a drug and diluent in a sealed, sterile environment. One type of device utilizes a dual-compartment syringe. One compartment of the syringe contains the diluent, and the other compartment contains the drug. The sidewall of the syringe contains a groove just forward of the stopper between the chambers. As a plunger is pushed through the syringe, the groove allows fluid to leak into the drug chamber. The drug and diluent are combined as the fluid from the diluent chamber enters the drug chamber, and then the injection is administered. The disadvantages of this method include use of a non-custom syringe and an often insufficient physical mixing of the drug and diluent.

Another device utilizes a "bottomless vial" concept for mixing drugs with diluents before administration. This concept requires the drug manufacturer to place a drug inside a bottomless vial. A second bottomless vial filled with a liquid diluent is connected adjacent to the bottomless vial containing the drug. By creating pressure in the liquid diluent vial with a plunger, the fluid is transferred into the drug vial. The plunger is then disconnected from the diluent vial and re-attached to the vial now containing drug and diluent. A needle is also attached to the drug/diluent vial and after mixing, an injection is administered. The disadvantages of this method include the use of non-custom vials, a possible exposure of the drug/diluent to the environment, and manipulation steps which may be burdensome to some users.

SUMMARY OF THE INVENTION

The present invention provides devices and methods for mixing a formulation containing two or more constituents, such as a drug composition and a diluent to solubiilze the drug for injection into a patient. The constituents can also be two or more liquids, or a combination of liquids and solids or semi-solid materials (e.g., a lyophilized product), etc. Other aspects of the invention provide methods for mixing two constituents using a device.

In one embodiment the present invention provides a device for mixing a formulation. The device has two or more sides that are connected by a hinge and having an open position and a closed position, the two or more sides defining a chamber between them for securing a container when the sides are in the closed position. When the device is in the open position a container can be placed into the chamber. The device also has a handle connected to at least one of the two or more sides for manipulation of the device after insertion of the container. In one embodiment the device has a container present within the chamber. The container can be a vial containing a drug and/or a diluent, and a syringe can be present inserted into the vial. In one embodiment the chamber has an opening, or an at least partially transparent portion, through which the container is visible from the exterior of the device. The chamber can be sized and shaped to secure the container. By "sized and shaped" is meant that the chamber has dimensions that conform to the shape of the container contemplated for use with the device. When a container is placed in a chamber that is "sized and shaped" to the container, the container lies in the chamber securely and does not substantially move within the chamber. The container can be a vial. By "vial" is meant a small closed or sealable vessel for containing a composition. The composition can be in any form, for example a powder, crystal, liquid, or semi-liquid. In one embodiment the composition is a constituent of a drug product. The drug product can be a composition for injection into a patient. By "secure" the container is meant that when the container is in the chamber and the device is in the closed position, the container does not substantially move in response to manipulation of the device. Rather the motion of the device is translated into movement of the composition within the container. In one embodiment the movement of the container within the chamber is less than or equal to 2 mm when the device is manipulated. In other embodiments the movement of the container within the chamber is less than 3 mm or 5 mm when the device is manipulated. In one embodiment a syringe is a standard medical use syringe for injecting formulations into a patient, and the syringe has a needle for piercing the skin, a lumen for storing formulation for injection, and a plunger for expelling formulation from the lumen of the syringe.

In one embodiment the two or more sides are two opposing sides movable about the hinge from the open to the closed position. In one embodiment the hinge separates the two sides at an angle of up to 180 degrees. The chamber can be sized and shaped to accommodate a vial having a stopper to prevent the spilling of liquids from the vial, and/or an adaptor. The two or more sides can also be present as trays for securing the container in the device. The adaptor allows the insertion and connection of a syringe to the vial so that liquid can pass from the syringe to the vial without leakage of liquid. The container can be a vial and the chamber can be sized and shaped to secure the container and the syringe.

In another aspect the invention provides a device having a housing with two or more side bars defining a chamber for securing a container inside. The container can be visible from outside the housing between two side rails of the device. The chamber has a proximal and a distal end, and a stopping element at the distal end and is open on the proximal end. The stopping element provides a distal end of the chamber and prevents the container from being inserted any further into the chamber. The device can also have a handle comprising two arms that are connected to the chamber on the open end. The container can be inserted into the chamber through the open end between the two arms. In one embodiment the device has a container within the chamber. In other embodiments the container can be a vial containing a drug product. A syringe having a plunger can be inserted into the vial. The plunger of the syringe can extend from the open and proximal end of the chamber. In one embodiment the device has a housing with four side bars. But in other embodiments the housing has three side bars, or has two side bars that are of sufficient width to retain the container within the chamber. In other embodiments the housing has more than four side bars. In one embodiment the side bars lie parallel to each other. In one embodiment of the device the container is visible within the chamber between two or more of the side bars.

In another aspect the invention provides a device having a first member and a second member, the first member containing two or more prongs extending from a base on the first member and the second member containing two or more tubes extending from a base on the second member. The device has a first open position where the two members are separated, and a second closed position where the prongs and tubes are fitted together in a complementary fashion to form a chamber within for securing a container. The tubes can define the lateral boundaries of the chamber. In one embodiment the container is a vial, which can also have an inserted syringe having a plunger for expelling material from the syringe. The plunger of the syringe can protrude from an end of the device when the container and syringe are present in the chamber and the device is in the closed position. In one embodiment the container is visible between the tubes of the device when the device is in the second position. The chamber can be substantially tubular in shape.

In another embodiment when the device is in the second closed position the prongs abut against the base of the second member, and the tubes abut against the base of the first member.

In another aspect the present invention provides methods of mixing a formulation. The methods involve placing the formulation into a container, inserting the container into a device as described above, placing the device into the closed position, and shaking the device to mix the formulation. In one embodiment the placing the formulation into the container involves injecting a diluent into the container with a syringe.

In another aspect the invention provides methods of preparing a formulation. The methods involve placing the formulation into a container, inserting the container into a device as described above, and shaking the device to prepare the formulation.

DETAILED DESCRIPTION OF THE INVENTION

Embodiments of the present invention provide a device that addresses the difficulty users have during the preparation of an active agent for administration. Embodiments generally provide a tool for facilitating the mixing of a formulation containing two or more components, such as a drug with a diluent, two liquids, a liquid and a solid or semi-solid material (e.g., a lyophilized product), or combinations thereof. In one embodiment, the device facilitates the resuspension of microspheres in a diluent. Embodiments of the invention also generally provide an ergonomic handle to facilitate a shaking motion of the device by the user.

Generally, embodiments of the invention provide a device comprising a chamber and a handle connected to the chamber. In embodiments, the chamber comprises a housing having walls that define a lumen. In one embodiment, the chamber consists of a tubular lumen, or a lumen with a circular or elliptical cross-section. In other embodiments, the chamber is tubular for a portion of its length. Embodiments include a stopping element at one end of the chamber. In embodiments, the chamber is open on the end opposite to the end with the stopping element, such that a container is capable of being inserted into the chamber through the open end. The stopping element includes any member connected to the chamber that is capable of stopping a container from passing through the chamber past the stopping element at a stopping point. In one embodiment, the stopping element can be a polymer cap affixed to one end of the chamber. In another embodiment, the stopping element can be one or more protruding members extending into the chamber lumen. In yet another embodiment, the stopping element can be provided by a tapered chamber lumen with a smaller inner diameter at the stopping point than the inner diameter at the open end.

A handle is capable of being connected to or integrated with the chamber in some embodiments of the invention. One embodiment consists of an ergonomic handle comprising first and second opposing surfaces. In such an embodiment, at least one of the opposing surfaces is movable from a first position to a second position in which the first opposing surface is brought closer to the second opposing surface. The handle can be constructed with similar materials which comprise the chamber, but is not limited to materials used in the construction of the chamber. In embodiments, at least a portion of the handle is movable from a first position to a second position such that the open end of the attachable chamber remains open when the handle is in a first position, and the container inserted in the chamber is capable of being restrained when the handle is in a second position. In one embodiment, a container inserted in the chamber is restrained when the opposing surfaces are moved to a position parallel to the longitudinal axis of the housing. In another embodiment, the opposing surfaces of the handle can be reversibly locked when moved from a first position to a second position. In such an embodiment, the handle may be locked using a clamp. Another embodiment would allow a user to release tension from the handle and still restrain a container in the chamber of the device. To prevent accidental dropping, embodiments of the device may also include a wrist wrap to secure the grip of a user holding the handle. Furthermore, in various embodiments, the handle can include features such as ribs to assist with handling. Additionally, in other embodiments the handle can have a contour which conforms the fingers of a human hand to further assist with handling.

The devices provided by embodiments of the present invention secure and restrain the syringe/vial adaptor/vial apparatus within the mixing tool. The vial, and hence its contents, is generally positioned within the mixing tool such that it is exposed to the maximum amount of mixing motion. In one embodiment, a vial containing a mixture of diluent and microspheres is physically located in a chamber at a distal end of the mixing tool. The distal end of the device is exposed to the largest momentum changes when shaking the tool, thus facilitating mixing of the microspheres and diluent.

The device of the present invention may be manufactured by plastic injection molding as a continuous body or as individual parts which can be assembled. In some embodiments, the device can be manufactured as a packaging unit for a drug and diluent which can be opened and closed in a clamshell configuration. In such embodiments, the device may be constructed using any suitable manufacturing methodology, such as vacuum thermoforming to create a continuous body capable of holding an pre-packaged apparatus comprising a vial with one or more drugs, a vial adapter, and a syringe with a diluent. These embodiments could be made from a semi-transparent material, such as PETG, that would allow adequate visibility of the tray contents while the tray is in the closed configuration. In another embodiment, the housing of the device comprises a cage consisting of a tubular lumen and one or more sliding members for at least a portion of its length. The cage in this embodiment can serve as a housing for a vial-syringe assembly. In such an embodiment, a handle comprising a sleeve can be configured to slide over the cage. The handle can slide over a portion of the cage and become reversibly locked. In another embodiment, the handle can comprise a tube which is configured to slide onto the housing, which comprises a tubular lumen of a smaller diameter than the lumen of the handle. Other embodiments can include a chamber lumen designed to hold pens, other reconstitution containers, or various configurations of vial/vial adapter/syringe combinations.

In another embodiment, the device comprises a composite housing having a first section and a second section fitting together in a complementary fashion to form a chamber for containing a container-syringe assembly. The housing sections can be affixed together in a closed configuration by a pin and hole arrangement, by snap-fitting, or by other suitable mechanisms know in the art. In one aspect, the chamber is tubular, optionally, with a larger cross section at one end that an other to form a gripping section. When the device is in a closed configuration, a user can grip the gripping section.

Embodiments of the invention also provide methods for using the described devices to physically mix two compositions such a as a drug and a diluent. In one embodiment, an apparatus containing a drug and diluent is placed and secured within the mixing tool. A user then grabs the handle, and shakes the mixing tool, causing the apparatus with drug and diluent to be shaken simultaneously and consistently. The device of the present invention can be used in any delivery system that requires handling of an apparatus consisting of two or more compositions to be physically mixed. Embodiments may be used to physically mix two compositions such as two liquids, a liquid and a solid or a semi-solid material, or a liquid and a lypholized product. In one embodiment, the invention provides a method for mixing a first solution with a second solution or with a solid or semi-solid material, comprising inserting a container comprising the first solution and the second solution or solid or semi-solid material in a device comprising a chamber and handle, restraining the container in the chamber by moving the handle to the second position holding the handle after moving the handle to the second position; and shaking the apparatus in the chamber by shaking the handle. Some embodiments of the device may be capable of being held without the presence of a handle. In such embodiments, a user is capable of holding a distal end of the device away from the inserted container comprising the first solution and second solution, solid, or semi-solid material.

Figure 1:
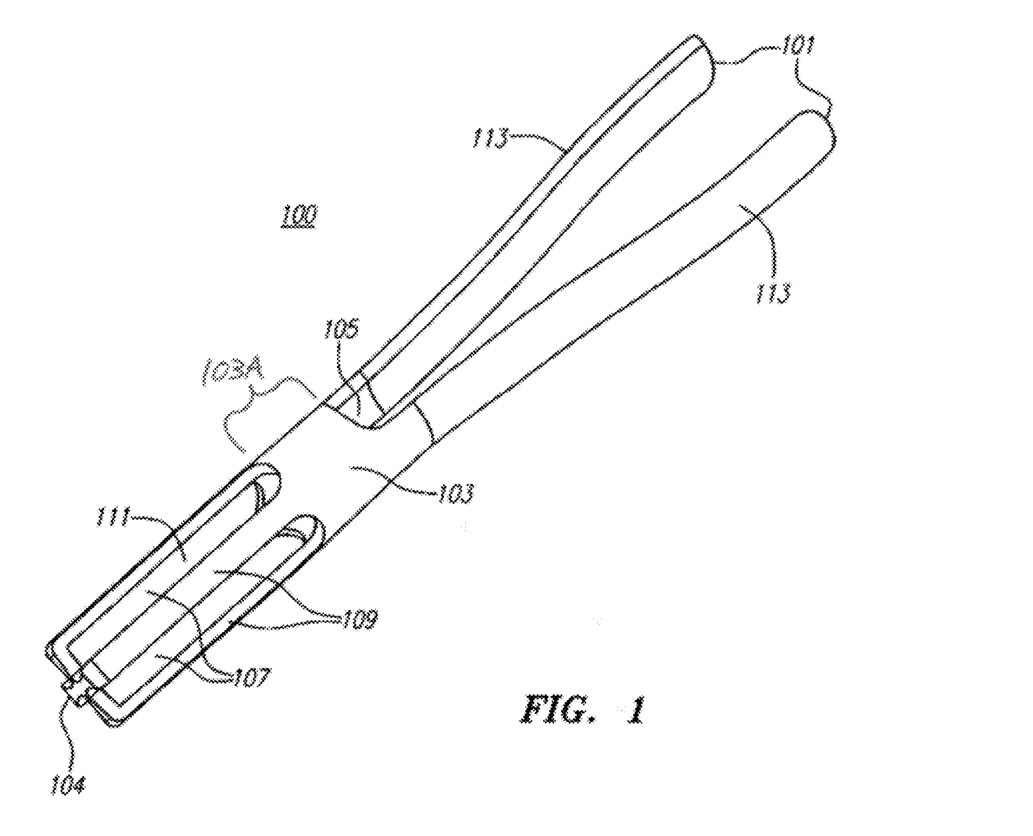
FIG. 1 exhibits a device according to one embodiment of the invention.

FIG. 1 provides an illustration of an embodiment of the present invention. In this embodiment the device includes a housing 103 including an annular portion 103A. The device contains a chamber 111 for securing a container inside. Sidebars 109 define the space of the chamber 111. When the container is present in the chamber 111 it is visible from the exterior of the device through the space 107 between the sidebars 109. The device contains an open end 105 and a stopping element 104 that supports the container in the chamber and stops it from being further introduced into the chamber. The housing 103 is rigidly connected to a handle 101 that has two arms 113. The container is inserted into the device through the open end 105 located between the two arms 113. In the embodiment depicted the device contains four sidebars 109.

Figure 2:
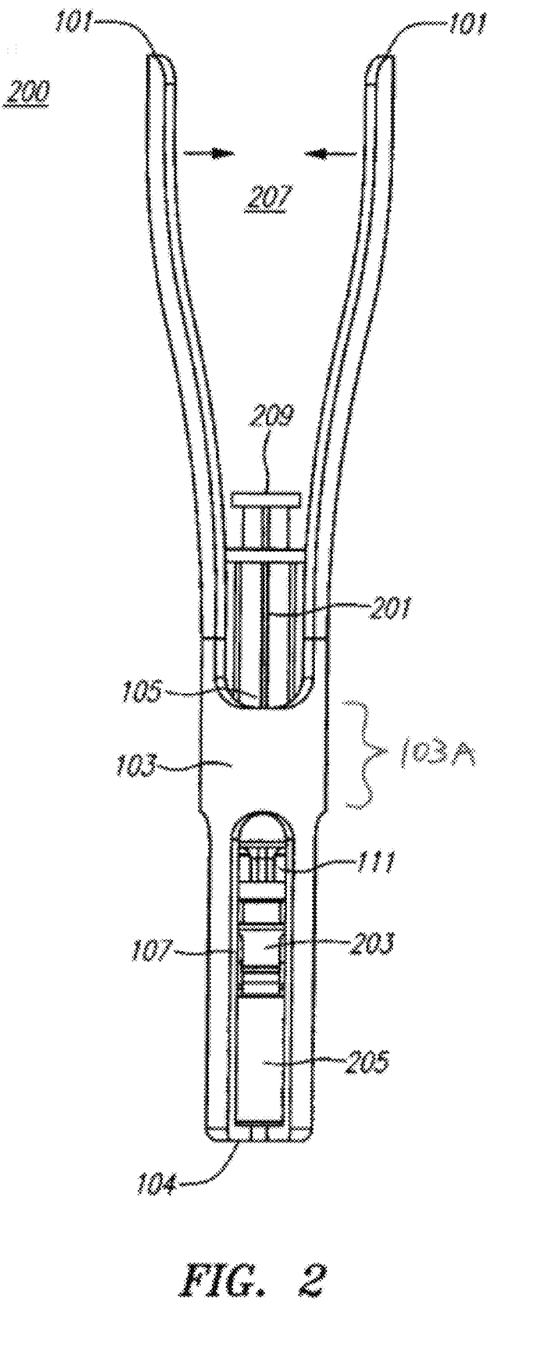
FIG. 2 exhibits a device according to one embodiment of the invention.

FIG. 2 provides an illustration of an embodiment of the device of the invention showing a side view. There is visible the housing 103 including the annular portion 103A, and window 107 allowing viewing of the chamber 111. The stopping element 104 is also visible, and the open end 105. In this Figure is shown a pre-packaged apparatus consisting of a syringe 201, having a plunger 209, and a vial adapter 203, and a vial 205 is inserted into the housing 103. When both arms of the handle are compressed according to a direction 207, the syringe 201, vial adapter 203, and vial 205 are restrained in the housing 103. In different embodiments, the housing 103 has a diameter of about 0.25 inches to about 0.75 inches, and the walls of the housing 103 have a thickness of about 0.1 inches to about 0.3 inches. In one embodiment, the diameter of the housing 103 is 0.5 inches, and the walls of the housing 103 have a thickness of 0.125 inches. Also in various embodiments the length of the device 200 can be from about 3.5 inches to about 15 inches. In one embodiment, the length of the device 200 is about 10 inches.

Figure 3:
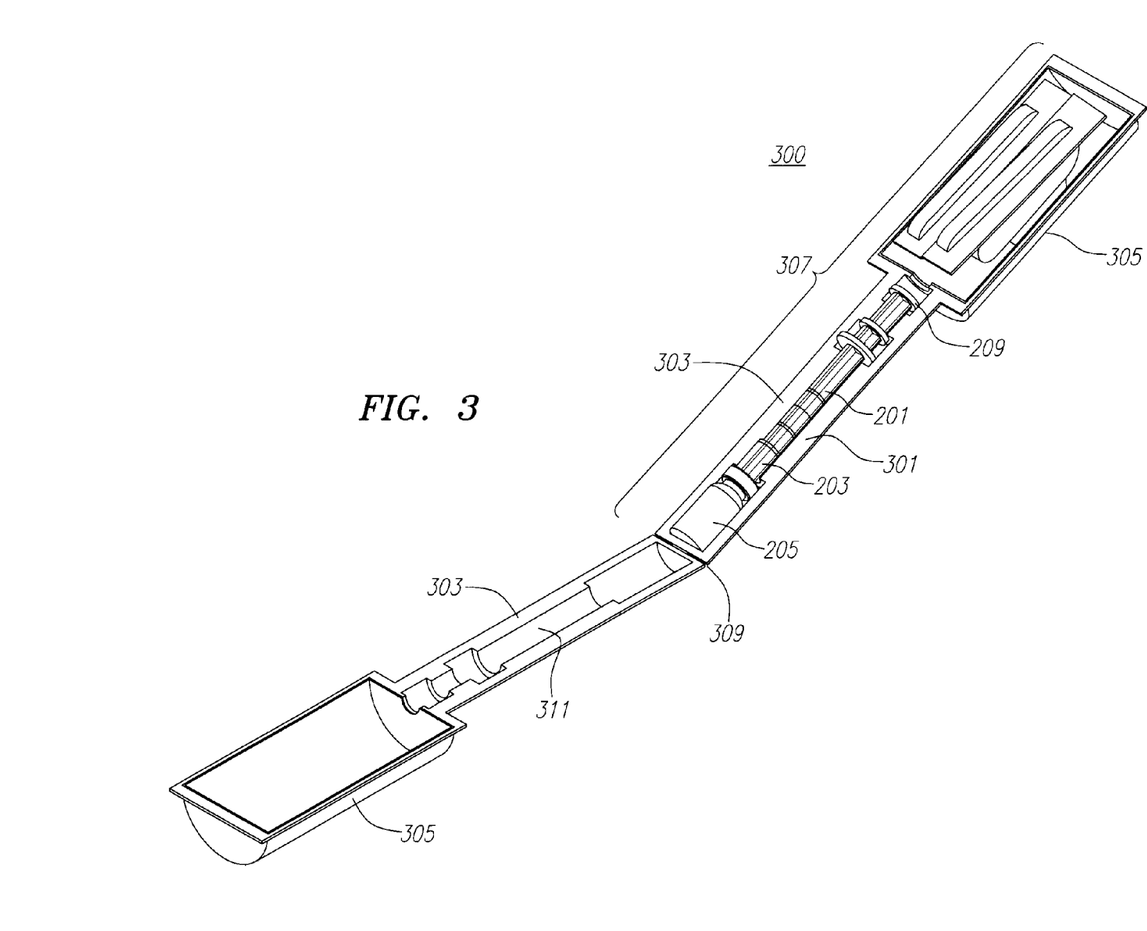
FIG. 3 exhibits a device according to one embodiment of the invention.

With reference to FIG. 3 there is depicted an embodiment of the device 300 of the invention. The device 300 includes two or more sides 303 that are connected by a hinge 309. The device is depicted in an open position. In the closed position the sides 303 define a chamber 311 between them for securing a container, such as a vial. The device also contains a handle 305 that is easy to grasp when the device is in the closed position. In this embodiment the side of the device pivots 180° about the hinge 309 to form an enclosed chamber in a closed configuration. In this depiction a container is present within the chamber 311 as a pre-packaged apparatus consisting of a syringe 201 having a plunger 209, a vial adapter 203, and a vial 205. When the device 300 is moved to the closed position, the syringe 201, vial adapter 203, and vial 205 are secured within the housing 301. In one embodiment, the handle 305 in a closed configuration can be used to store components accompanying a vial/syringe assembly, such as gauze, pre-packaged needles, or other materials useful for the operation of the device or use of the composition present in the container.

Figure 4:
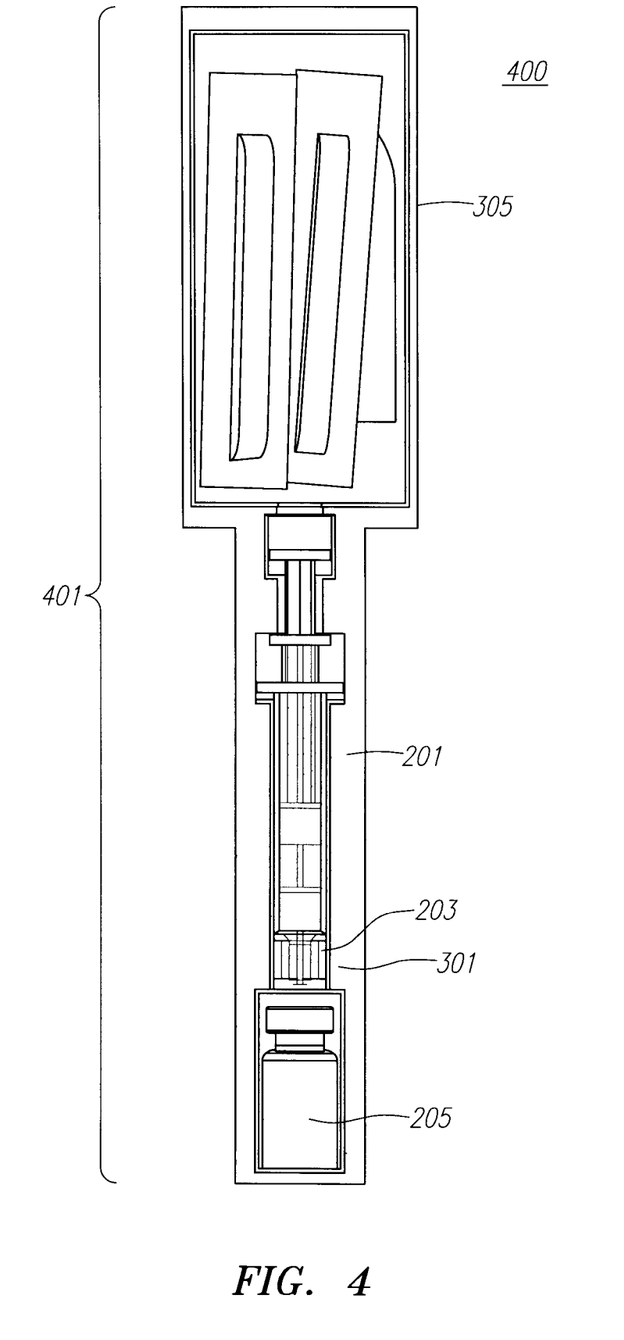
FIG. 4 exhibits a device according to one embodiment of the invention.

FIG. 4 depicts a cross-sectional view of the device in the closed position. The device has a handle 305 that is easy to grasp when the device is in the closed position. There is depicted within the device a pre-packaged apparatus consisting of a syringe 201, a vial adapter 203, and a vial 205 secured within the housing 301. In one embodiment the diameter of the housing 301 is approximately 0.5 inches, the diameter of the handle 305 is approximately 1.5 inches, and the length of the device 401 is approximately 10 inches. In the closed configuration of some embodiments, the handle 305 comprises a cylindrical cavity with a diameter of from approximately 1 inch to approximately 3 inches, and a length of from approximately 2 inches to approximately 5 inches. The device has a length of from approximately 3.5 inches to approximately 15 inches in some embodiments. In one embodiment, the length of the device is 9 inches.

Figure 5:
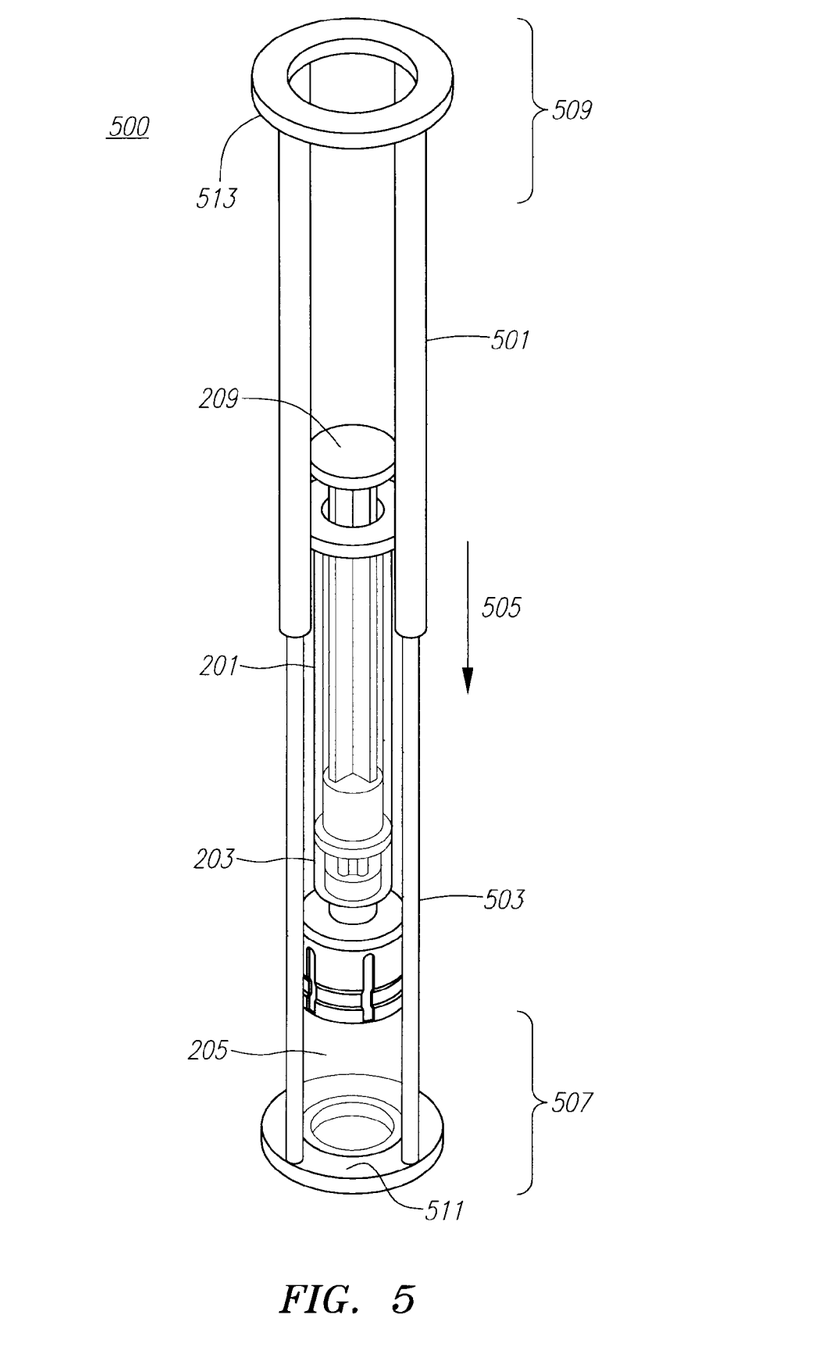
FIG. 5 exhibits a component of a device according to one embodiment of the invention.

With reference to FIG. 5 there is provided another embodiment of the device. In this embodiment the device has a first member 507 and a second member 509. The first member 507 has two or more prongs 503 that extend from a base 511 on the first member. The second member 509 has two or more tubes 501 that extend from a base 513 on the second member. The device is depicted in a partially open position. In the open position the first and second members are separated. In the second position the prongs of the first member and the tubes of the second member are fitted together in a complementary manner to form a chamber within. In such embodiment the tubes 501 define the lateral boundaries of the chamber. The device is depicted with a prepackaged apparatus present within the chamber including a syringe 201 having a plunger 209, a vial adapter 203, and a vial 205 inserted into the chamber. In the closed position the syringe 201, vial adapter 203, and vial 205 are secured within the chamber. In the closed position the prongs abut against the base of the second member, and the tubes abut against the base of the first member. In other embodiments the closed position is configured so that the base 511 on the first member and the base 513 on the second member are drawn to within a convenient distance of one another and can be easily manipulated or shaken by the user. In such embodiments the prongs may not abut against the base of the second member and the tubes may not abut against the base of the first member. In various embodiments the base on the first member and the base on the second member are drawn to within 6 inches of one another, or within 7 inches of one another or within 8 inches of one another.

Figure 6:
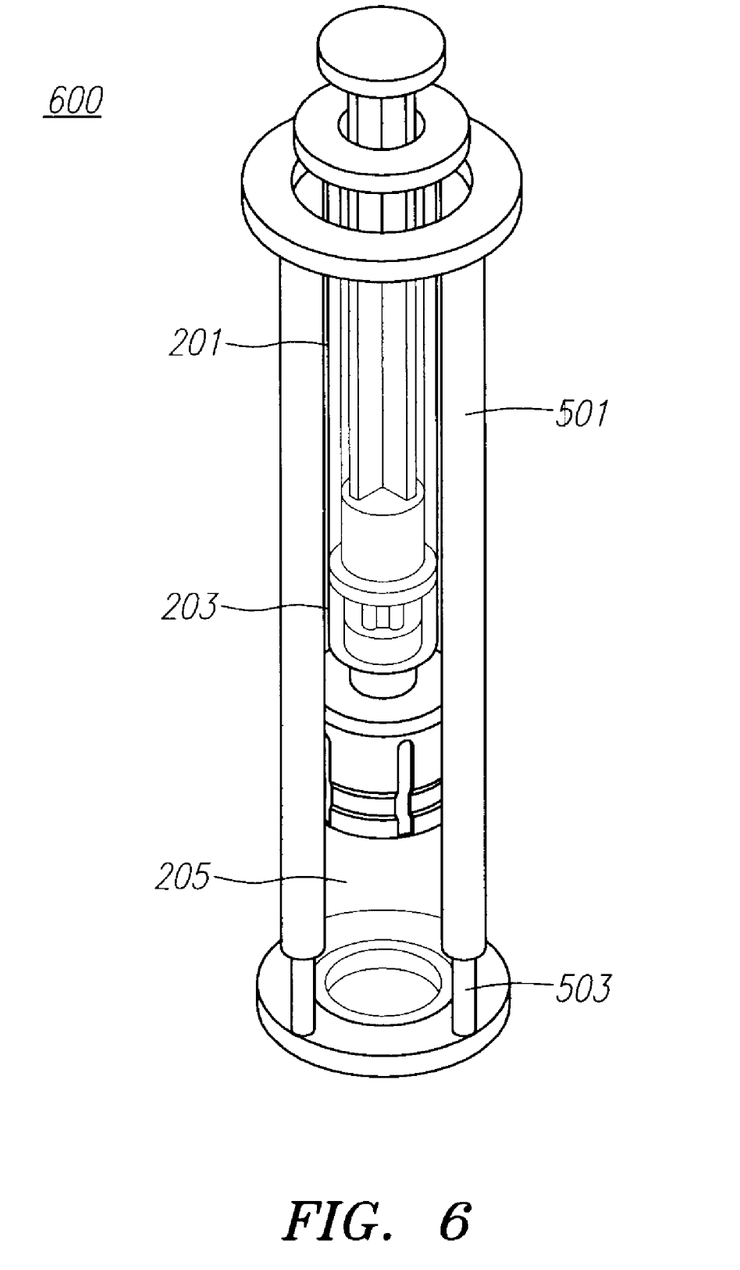
FIG. 6 exhibits a component of a device according to one embodiment of the invention.

FIG. 6 provides another view of the device according to one embodiment of the present invention. A prepackaged apparatus including a syringe 201, a vial adapter 203, and a vial 205 is inserted into the chamber. The tubes 501 are placed on the prongs 503 such that the syringe 201, vial adapter 203, and vial 205 are restrained within the chamber.

Embodiments for practicing the present invention have been described. It will be understood and readily apparent to the skilled artisan that many changes and modifications may be made to the above-described embodiments without departing from the spirit and the scope of the present invention. The foregoing is illustrative only and that other embodiments may be employed without departing from the true scope of the invention defined in the following claims.

The invention claimed is:

1. A device comprising:
    a housing comprising an annular portion and a plurality of side bars extending from the annular portion, the annular portion and the plurality of side bars defining a chamber for securing a container therein, the container visible from outside the housing between at least two side bars of the plurality of side bars;
    a stopping element at one end of the chamber to support the container in the chamber, the chamber being open at an open end of the annular portion opposite the one end; and
    a handle comprising two arms extending from the annular portion,
    wherein the handle is movable between a first position in which the container is insertable into the chamber through the open end of the annular portion between the two arms, and a second position in which distal ends of the two arms are nearer to one another relative to the first position for securing the container in the chamber.

2. The device of claim 1, wherein the two arms are substantially parallel to a longitudinal axis of the housing when the handle is in the second position.

3. The device of claim 1, wherein the handle is reversibly lockable when moved from the first position to the second position.

4. The device of claim 1, wherein the stopping element includes portions of respective ones of the side bars that are bent toward one another at the one end.

5. The device of claim 1, wherein the chamber is substantially tubular.

6. The device of claim 1, wherein a first end of the chamber is larger than a second end of the chamber.

7. The device of claim 1, wherein the housing has a diameter of about 0.25 inches to about 0.75 inches.

8. The device of claim 1, wherein at least two side bars of the plurality of side bars are spaced apart to define an opening therebetween to an outside of the device.

9. The device of claim 1, wherein the housing comprises four of the side bars.

10. The device of claim 9, wherein the container is visible within the chamber between pairs of adjacent side bars of the side bars.

11. A device comprising:
    a housing comprising an annular portion and a plurality of side bars extending from the annular portion, the annular portion and the plurality of side bars defining a chamber, the chamber being open at an open end of the annular portion;
    a container in the chamber, the container visible from outside the housing between two of the side bars;
    a stopping element at an end of the chamber opposite the open end, the stopping element supporting the container in the chamber; and
    a handle comprising two arms extending from the annular portion,
    wherein the handle is movable between a second position in which the container is secured in the chamber, and a first position in which the container is removable from the chamber through the open end of the annular portion between the two arms, distal ends of the two arms being nearer to one another in the second position relative to the first position.

12. The device of claim 11, wherein the two arms are substantially parallel to a longitudinal axis of the housing when the handle is in the second position.

13. The device of claim 11, wherein the stopping element includes portions of respective ones of the side bars that are bent toward one another at the end of the chamber opposite the open end.

14. The device of claim 11, wherein a portion of the container extends from the open end of the chamber and is restrained between opposing surfaces of the two arms when the handle is in the second position.

15. The device of claim 11, wherein the container comprises a vial containing a drug, and wherein a syringe comprising a plunger is coupled to the vial, the plunger of the syringe extending from the open end of the chamber.

16. The device of claim 15, wherein the vial is at a distal end of the chamber relative to the handle.

17. The device of claim 15, wherein the drug in the container comprises two or more compositions that are physically mixable when the device is shaken.

18. The device of claim 17, wherein the two or more compositions comprise a diluent and microspheres.

19. A device comprising:
 a housing defining a chamber for securing a container therein;
 a stopping element at one end of the chamber to support the container in the chamber, the chamber being open at an open end opposite the one end; and
 a handle comprising two arms extending from the housing,
 wherein the handle is movable relative to the housing between a first position in which the container is insertable into the chamber through the open end between the two arms, and a second position in which the two arms are compressed in a direction toward one another relative to the first position for securing the container in the chamber.

20. The device of claim 19,
 wherein the housing comprises an annular portion, and a viewable portion extending from a first end of the annular portion toward the one end of the chamber, the container being visible in the viewable portion from outside the housing, and
 wherein the handle extends from a second end of the annular portion opposite the first end.

* * * * *